(12) United States Patent
Whipp

(10) Patent No.: US 9,387,113 B2
(45) Date of Patent: Jul. 12, 2016

(54) ORTHOPAEDIC WALKER

(75) Inventor: Christopher Whipp, Epsom (GB)

(73) Assignee: SONOA PRODUCTS LTD, Epsom (GB)

( * ) Notice: Subject to any disclaimer, the term of this patent is extended or adjusted under 35 U.S.C. 154(b) by 409 days.

(21) Appl. No.: 13/816,225

(22) PCT Filed: Aug. 8, 2011

(86) PCT No.: PCT/GB2011/051499
§ 371 (c)(1),
(2), (4) Date: Feb. 8, 2013

(87) PCT Pub. No.: WO2012/020251
PCT Pub. Date: Feb. 16, 2012

(65) Prior Publication Data
US 2013/0144200 A1 Jun. 6, 2013

(30) Foreign Application Priority Data
Aug. 9, 2010 (GB) .................................. 1013334.6

(51) Int. Cl.
*A61F 5/00* (2006.01)
*A61F 5/01* (2006.01)
*A61F 5/058* (2006.01)

(52) U.S. Cl.
CPC ............... *A61F 5/0195* (2013.01); *A61F 5/012* (2013.01); *A61F 5/0585* (2013.01)

(58) Field of Classification Search
CPC . C08L 2666/02; C08L 2666/24; C08L 53/02; C08L 53/025; C08L 2666/04; C08L 23/06; C08L 23/30; C09J 153/02; C09J 153/025; A61F 5/0111; A61F 2/7812; A61F 2/7843; A61F 2/80; A61F 5/0127; A43B 13/04; A43B 13/16; A43B 23/027; A43B 5/00; A43B 7/22; A43B 13/183; A43B 13/184; A43B 13/36; A43B 1/0081; A43B 21/26; A43B 23/042; A43B 23/24; A43B 3/0078; A43B 3/128
USPC ........................................ 602/23, 27; 128/882
See application file for complete search history.

(56) References Cited

U.S. PATENT DOCUMENTS

| | | | | |
|---|---|---|---|---|
| 4,446,856 A | * | 5/1984 | Jordan | 602/27 |
| 4,505,057 A | * | 3/1985 | Kiester | 36/117.4 |
| 5,088,481 A | * | 2/1992 | Darby | 602/23 |
| 5,425,701 A | * | 6/1995 | Oster et al. | 602/23 |
| 5,761,834 A | * | 6/1998 | Grim et al. | 36/88 |
| 5,940,992 A | * | 8/1999 | Darby | 36/110 |
| 7,004,918 B2 | * | 2/2006 | Rolnick et al. | 602/30 |
| 2009/0043234 A1 | | 2/2009 | Bledsoe et al. | |

FOREIGN PATENT DOCUMENTS

EP 1488715 B1 9/2006
WO WO 92/08382 A1 5/1992

* cited by examiner

*Primary Examiner* — Michael Brown
(74) *Attorney, Agent, or Firm* — Roberts Mlotkowski Safran Cole & Calderon, P.C.

(57) ABSTRACT

The invention relates to walkers, and in particular, to orthopaedic walker devices for assisting in the stabilization and healing of injuries to the lower leg and/or foot, including fractures to the bones of the foot, such as metatarsal fractures, 'Jones Fracture or broken phalanges.

6 Claims, 1 Drawing Sheet

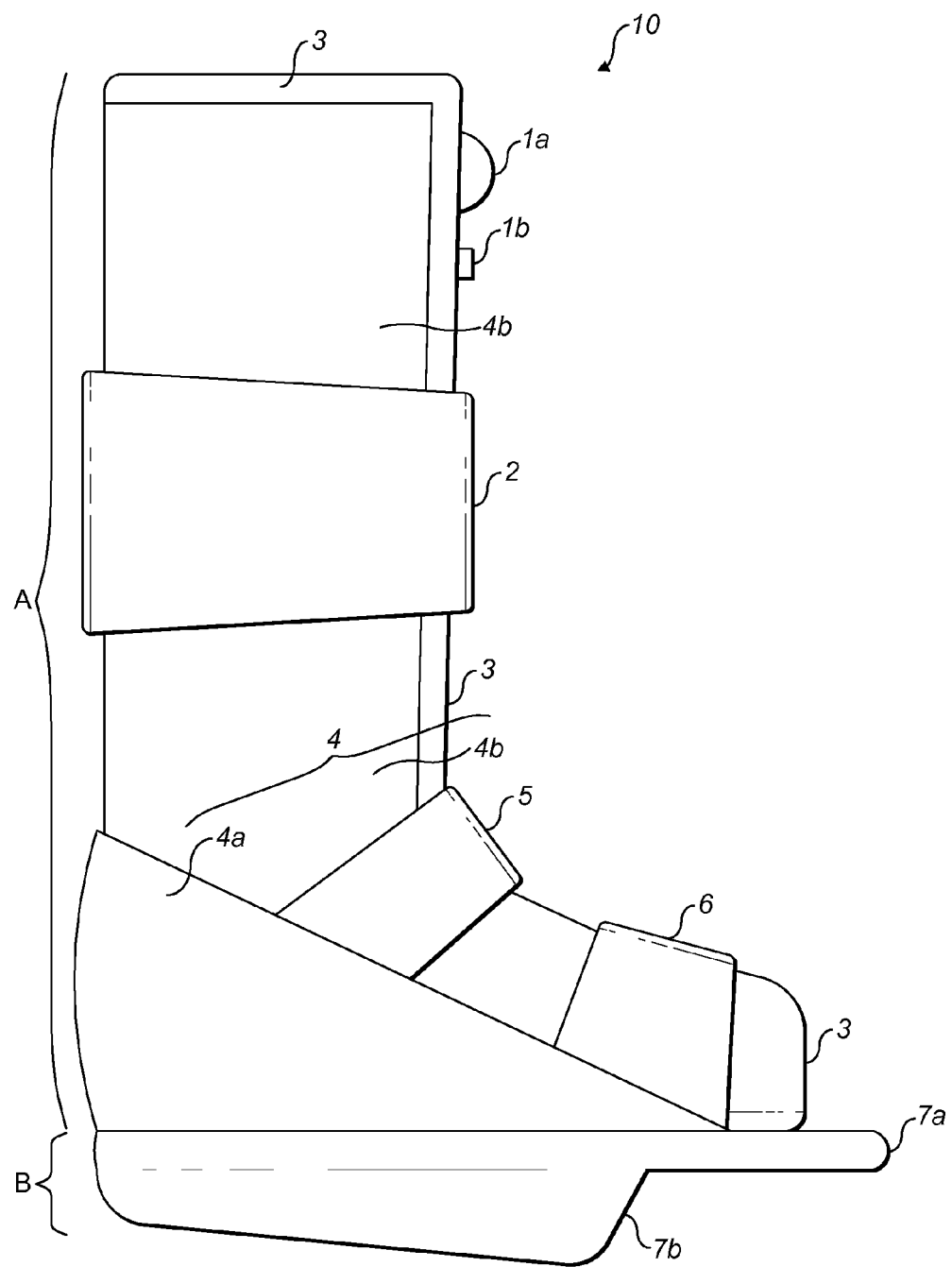

ORTHOPAEDIC WALKER

This application is the National Phase Under 35 U.S.C. §371 of PCT International Application No. PCT/GB2011/051499 which has an International filing date of Aug. 8, 2011, which claims priority under 35 U.S.C. §119 to United Kingdom Application No. 1013334.6 flied on Aug. 9, 2010. The entire contents of all applications listed above are hereby incorporated by reference.

The present invention relates to orthopaedic walkers, and in particular, to orthopaedic walker devices for assisting in the stabilization and healing of injuries to the lower leg and/or foot, including fractures to the bones of the foot, such as metatarsal fractures.

In order to aid in the proper healing and treatment of lower leg and foot injuries, it is necessary that the affected areas, as well as the surrounding tissue, are compressed and immobilised. Plaster or synthetic casts have long been used for this purpose. However, casts may be associated with a number of drawbacks. For example, when the swelling caused by trauma or surgery subsides, the cast may become loose, reducing the effectiveness at compressing and/or immobilizing the affected area. A loose cast may also directly cause discomfort.

In addition, casts may trap drainage from wounds in the cast padding, increasing the chance of infection, which cannot be easily treated since casts must be removed in order to treat or cleanse a wound. Casts may also irritate the skin, and, due to the water-sensitive nature of the casting material, casts also prevent bathing. Furthermore, cast removal and replacement can only be performed by skilled persons in specialised clinics. The need for repeated visits to the clinic increases the expense of the treatment and is time consuming for the patient.

For these reasons, casts are increasingly being replaced, in treatment, by a combination of bandages and walker immobilization braces. Such braces, often referred to as "walker boots" or "walkers", typically comprise a boot portion designed to fit around the patient's foot and lower leg, and a rigid rocker sole designed to allow the patient to roll through a gait cycle while immobilizing the ankle, foot and metatarsal-phalangeal joint. The walker sole is configured to provide a weight-bearing surface to the sole of the foot across which pressure is exerted uniformly.

However, some conditions, including fractures of the small bones of the foot, such as Jones fractures and other metatarsal injuries, cannot be treated using a walker, since it is important for the healing process that pressure is not exerted on the affected area of the foot. For this reason, treatment of metatarsal fractures, which account for over 10% of traumatic foot injuries, continues to involve the use of a cast, in combination with weight bearing the patient with crutches as pain permits. This approach generally allows recovery in about 6 weeks. In comparison to the treatment of other fractures, this approach is considered time-consuming, expensive and debilitating.

Wedged-sole, or "offloader", surgical shoes are known for use in the treatment of conditions affecting the sole or plantar surface of the foot, such as plantar ulceration which is a common complication of diabetes and other neuropathic conditions. However, such shoes are not suitable for use in the treatment of fractures to bones of the foot, such as Jones fractures and other metatarsal injuries. Firstly, offloader shoes do not offer any compression or immobilization to the affected area, and therefore do not promote healing. Secondly, being soft, and only covering a portion the foot, such offloader shoes do not offer patients the sensation of protection and visibility of the foot injury. This is exacerbated by the fact that when using such a shoe to exert pressure on the injured foot, patients would not also require the use of crutches to alert others to their injury.

There is therefore a need for improved walkers, for use in treating foot injuries such as metatarsal injuries.

In a first aspect, there is provided an orthopaedic walker comprising a compression walker boot and an offloader sole.

Known walker boots are used for the treatment of various lower limb injuries and post-op treatment. Offloader soles are currently found on 'offloader shoes', which are generally used in the treatment of plantar ulceration and other injuries to the surface of the sole of the foot. Due to the nature of these injuries, and to prevent further damage to the foot surface, offloader shoes are soft and padded. In particular, known offloader shoes do not offer any compression or immobilisation to the foot and would therefore generally be considered highly inappropriate for use in the treatment of fractures such as metatarsal fractures. In contrast, the compression and immobilisation provided by known walker boots means that patients do not require a permanent cast. However, known walkers typically have a curved sole that is intended to assist the gait cycle and to spread the weight bearing load evenly across the foot. As a result, however, known walkers are not suitable for use in treating fractures such as metatarsal fractures because the patient is not able to weight-bear sufficiently.

Combining the walker boot with an offloader sole to create the orthopaedic walker of the first aspect surprisingly increases the degree of weight-bearing that patients with such injuries are able to exert on the injured limb. The surprising benefit of this approach is that it provides a considerable reduction in recovery time, as well as reducing discomfort in a subject wearing a walker device. Furthermore, it also replaces the requirement for using a plaster cast and therefore reduces the cost, both in terms of the materials and expertise required in cast fitting and removal, and also the frequency of hospital visits for the patient.

The walker may be externally offloaded. Accordingly, it is preferred that the offloading system provided in the walker is not internal, for example by means of sections of the inner sole being modified to alter pressure distribution across the sole of the foot.

The offloader sole may be arranged, in use, to promote weight-bearing on or towards any particular portion of the foot of a subject wearing the walker, the portion of the subject's foot being selected according to the nature of the injury, and the type of treatment that is most suitable.

For example, in one embodiment, as shown in FIG. 1, the offloader sole may be arranged, in use, to promote weight bearing on or towards a rear portion of the sole of the foot of a subject wearing the walker. The rear portion of the foot may be the subject's heel. The sole of the walker may comprise a tapered portion, arranged to elevate the front, toe end of the foot. The tapered portion may be tapered so that the sole thickness (or vertical height) is reduced as it extends towards the rear of the foot. Thus, the offloading sole may comprise a wedge-shaped section having a narrow (or vertically shallow) end disposed at or towards the rear end of the sole and increasing in thickness (or vertical height) to a wide end disposed at or towards the front end of the sole. The wedge may or may not extend along the entire length of the sole. Preferably, the wedge does not extend to the end of the front of the sole, thereby offloading pressure, in use, away from the front of the foot, where the subject's toes would be positioned. The wide end of the wedge may be disposed at a position corresponding to 50%, 60%, 70%, 80% or 90% of the distance between the rear (i.e. heel) end and the front (i.e. toe) end of the sole. The narrow end of the wedge may be aligned with the rear end of the sole, corresponding to the position of the subject's heel. Advantageously, this embodiment is particularly useful for treating injuries to the forward part of the subject's foot, including the toes and metatarsals.

In another embodiment, the offloader sole may be arranged, in use, to promote weight bearing on or towards a front portion of the sole of the foot of a subject wearing the walker. The front portion of the foot may be the subject's toes or metatarsals. The sole of the walker may comprise a tapered portion, arranged to elevate the rear, heel end of the foot. The tapered portion may be tapered so that the sole thickness (or vertical height) is reduced as it extends towards the front of the foot. Thus, the offloading sole may comprise a wedge-shaped section having a narrow (or vertically shallow) end disposed at or towards the front end of the sole and increasing in thickness (or vertical height) to a wide end disposed at or towards the rear end of the sole. The wedge may or may not extend along the entire length of the sole. Preferably, the wedge does not extend to the end of the rear of the sole, thereby offloading pressure, in use, away from the rear end of the foot, where the subject's heel would be positioned. The wide end of the wedge may be disposed at a position corresponding to 50%, 60%, 70%, 80% or 90% of the distance between the front (i.e. toe section) and the rear (i.e. heel section) of the sole. The narrow end of the wedge may be aligned with the front end of the sole, corresponding to the position of the subject's toes. Advantageously, this embodiment is particularly useful for treating injuries to the rear part of the subject's foot, which may, for example, be following surgery to the soft tissue or bony structure of the heel.

The offloader sole may comprise an inner sole and a wedge-shaped undersole. The offloader sole may also comprise an inner sole. The inner sole is positioned on top of the mid-sole, and the wedge-shaped undersole may be arranged on the lower surface of the mid-sole. The undersole is wedge-shaped due to the upper surface of the undersole being inclined at an acute angle with respect to the base surface of the undersole. In use, the wedge-shaped undersole functions to incline the walker and thereby elevate the region of the foot on which the weight-bearing load is intended to be reduced. Preferably, the angle that is formed between the upper and lower surfaces of the undersole is from 5-35°, 10-25°, or 15-20°. For example, the upper surface of the undersole may create an angle of at least 2°, 3°, 4°, 5°, 10°, 15°, 20°, 25°, 30°, or 35° with respect to the base of the undersole. The mid-sole and undersole may be formed as a single section, or as individual sections which are subsequently bonded or fastened together. The mid-sole and undersole may be formed from similar or different materials. Suitable materials may be substantially inflexible, or may alternatively have a degree of flexibility. For example, the mid-sole and/or undersole may be formed from a material selected from the group consisting of: ethylene vinyl acetate; polyurethane or other plastic or thermoplastic; rubber, including thermoplastic rubber (TPR), styrene butadiene rubber and natural rubber; or any combination of these materials. The wedge-shaped undersole may occupy 50-90%, 55-80%, or 60-70% of the lower surface area of the mid-sole. For example, the wedge-shaped undersole may occupy at least about 35, 40, 45, 50, 55, 60, 65, 70, 75, or 80% of the lower surface area of the mid-sole. In some embodiments, the wedge-shaped undersole may occupy up to about 50, 55, 60, 65, 70, 75, 80, 85, 90, or 95% of the lower surface area of the mid-sole.

The sides of the wedge-shaped undersole may be substantially flat and vertical. In alternative embodiments, the undersole may be shaped so that the upper and lower surfaces are substantially larger than a central cross-section, such that the sides of the undersole are substantially concave.

The toe end of the mid-sole may extend to surround the front and sides of the toes, thereby protecting the toes. The mid-sole may have a circumferential lip or vertical ridge, which may function to retain the inner sole. The wedge-shaped undersole may comprise upper and lower surfaces which are both substantially flat. The flat base of the undersole means that in use, the base of the walker is placed on the ground and does not provide a rocker motion. In other embodiments, the base of the walker may be slightly curved, for example to assist the gait cycle.

The undersole may comprise one or more recesses, which may extend into the undersole from the upper surface, but generally, do not form openings in the base of the undersole, thereby forming sealed hollow cavities when the undersole is attached to the mid-sole. In this way, the recesses do not prevent the undersole from maintaining the desired portion of the foot in a raised position. The or each recess may reduce the weight of the walker and/or provide a degree of shock-absorption. The undersole may have a single large recess, a large number of small recesses, or a configuration of recesses between these two extremes.

It has been surprisingly found that the offloader sole of the walker of the invention may have a reduced thickness compared to previous offloader soles used in surgical shoes, for example in the treatment of diabetic plantar ulceration. Indeed, the thickness of the sole of the disclosed walker may be approximately equivalent to that of a conventional shoe or boot. This finding is particularly advantageous because the walker will generally only be worn on one leg and for an extended period of time. Thus, if the base is of a thickness that is significantly greater than the thickness of standard footwear, then the resulting continual uneven walking may be uncomfortable for the wearer.

The inner sole may be formed in a single section, and does not comprise, for example, removable sections to facilitate internal offloading. The inner sole may be formed from a shock absorbing foam material, to pad the plantar surface of the patient's foot to provide comfort and protection. In particular, the inner sole may be formed a microcellular foam, such as Plastizote (Plastizote is a medically inert, high density polyethylene closed cell foam having excellent memory and impact absorption properties), EVA, Poron (Poron is an impact absorbing open cell cellular urethane foam product), or other suitable material. The inner sole may comprise a plurality of layers. For example, the inner sole may have two layers. The upper layer may be made of a soft density EVA, and the lower layer of a medium density EVA. The insoles may be pressure mouldable and conform to the plantar aspect of the foot providing total contact with the sole of the foot and more comfort to the patient.

The compression walker boot may comprise a substantially compressible inner section and an outer shell, which may be substantially rigid. The purpose of the outer shell is to provide strength and stability to the walker. Accordingly, the outer shell may comprise polymeric material, which may be polyurethane, or alternatively, any material that is stiff, non-flexible, semi-flexible and/or has any degree of flexibility between these extremes, may be used, as appropriate. Alternatively, the outer shell may be composed of a natural material, such as leather. The outer shell may be formed from a single section of material, or by the combination of a number of individual sections of material, which may be similar materials or different materials. The outer shell may be injection-moulded.

The offloader sole may be attached to the base of the outer shell of the walker. For example, the upper surface of the mid-sole may be shaped to receive the outer shell of the walker. The undersole, mid-sole, and outer shell of the walker may be fixedly attached to one another, for example, by means of an adhesive and/or the use of rivets. In some embodiments, the undersole and mid-sole, or mid-sole and outer shell, may be integrally formed, for example, by injection moulding.

Conditions for which the walker is particularly suitable include fractures of the small bones of the front of the foot, such as Jones fractures and other metatarsal injuries. In this case, the undersole may be positioned on the base of the walker such that the narrower end of the wedge is aligned at the heel end of the walker. The broader (vertically higher) end of the wedge may be situated at a position towards the toe end of the walker. The upper surface of the undersole may be inclined at an acute angle with respect to the base, and, for example, the vertical height of the upper surface of the offloader sole at the toe end may be approximately 0.5, 1, 1.5, 2, 2.5, 3, 3.5, or 4 cm greater in height than at the heel end.

The outer shell may comprise an ankle stabilisation section and a leg stabilisation section. The ankle stabilisation section may have a first portion that forms part of the sole of the walker, and a second portion that preferably extends to encompass at least the height of the subject's heel. Advantageously, the ankle stabilisation section may offer increased support and stability to the ankle and lower leg, and prevent the subject's heel from slipping backward out of the walker. The ankle stabilisation section may be shaped to accommodate the medial and lateral ankle malleoli. For example, the internal surfaces of the ankle stabilisation section may comprise one or more concavities which correspond to the location of the ankle bones. The ankle stabilisation section may also extend to encompass the toes, such that the toes are completely contained within the boot. In other embodiments, the ankle stabilisation section does not encompass the toes, which are partially exposed. In some embodiments, the ankle stabilization section may be attached to the leg stabilisation section by glue or rivets. In other embodiments, the ankle and leg stabilisation sections may be formed as a single unit, for example by an injection moulding technique.

The leg stabilisation section may have a U-shaped cross section. Advantageously, the open front of the leg stabilisation section may provide support and stabilisation to the sides and rear of the subject's limb, while allowing the limb to be easily inserted into, and extracted from, the walker without the need for excessive handling and manipulation, which may be painful.

The top of the walker, in use, may extend to a distance between approximately 3, 4, or 5 cm above the subject's ankle and approximately 2 cm below the subject's knee. The walker may alternatively have any height in between these two extremes. In one embodiment, the walker may be a 'high top' walker, the top of which finishes just below the subject's knee, for example 2 cm below the knee of the subject. The height of the boot may be determined by the length of the leg stabilisation section. In other embodiments, the walker may be a 'low top' walker. The top of a low top walker may finish just above the ankle of the patient, for example about 3, 4, or 5 cm above the ankle. Generally, in the case of low top walkers, the ankle stabilisation section and leg stabilisation section of the walker are moulded as a single piece.

The walker may comprise a compression inner. Advantageously, the compression inner provides controlled, uniform compression of the patient's foot, ankle and leg, while reducing friction and generally ensuring that the walker fits comfortably around the lower leg and foot. The compression inner may comprise padding. The inner may be porous and therefore breathable, thereby providing ventilation to the limb, and reducing the overall weight of the walker. The inner may comprise a foam comprising ethylene vinyl acetate. The compression inner may be covered with an absorbable fabric, which may be loose weave. The fabric may be a natural fabric, such as cotton, or synthetic fabric, such as nylon or Lycra, or a combination or different types of fabrics may be used.

The compression inner may be removeably attached to the internal surface of the outer shell of the walker, for example by adjustable fastening means, examples of which may include hook and loop (Velcro). In some embodiments, the inner surface of the outer shell of the boot may comprise patches of Velcro-type nylon hooks, which may engage with the compression inner and stop it slipping within the boot. Removable attachment of the compression inner allows the patient to remove the leg from the boot, without relieving the compression of the injured limb. This arrangement may also allow the compression inner to be easily washed and/or replaced.

The compression inner may comprise one or more inflatable bladders, which, when inflated, may be arranged to provide compression and cushioning to the subject. A plurality of bladders, or a single bladder comprising a number of individual pockets, may be used. The inflatable bladder may be used instead of the foam of the compression inner, or in combination with the foam, such as between two foam layers for additional cushioning. The inflatable bladder may offer increased support to the limb, and the possibility of precisely controlling the level of compression. The inflatable bladder preferably provides compression to the majority of the limb, for example to at least 50%, 60%, 70%, 80% or 90% of the surface of the limb supported by the walker. The bladder may be constructed of a resilient material. For example, urethane may be used, or a rubber or SPANDEX may be used, with a urethane laminate coating on the inside. A urethane bladder with tricot material facing the ankle may also be used. The nature of the material used may depend, for example, on the size and shape of the bladder, and on the location of the bladder within the walker.

The inflatable bladder may be inflated using a fluid, which may be a gas or liquid. Preferably, the bladder may be inflated with air. The inflating fluid may have a temperature that is above or below ambient temperature. Hot/cold therapy may be advantageous in the healing process since it reduces swelling of the injured limb and it reduces the degree in which muscles in the injured limb may atrophy by promoting improved blood circulation throughout the lower leg. In use, after the limb is inserted into the walker, the bladder may be inflated until a comfortable, compressive fit is provided around the injured limb. The bladder may be inflated by any suitable means. In some embodiments one or two pumps are provided by which the bladder may be inflated. For example, a manual pump, such as a pump bulb, may be used. The bladder may comprise a valve for retaining the fluid therein, and for selective deflation.

The walker may be ventilated. For example, the outer shell and/or the compression inner may have one or more ventilation openings. The or each ventilation opening helps to regulate the temperature and humidity within the walker. In one embodiment, the ventilation opening may comprise an aperture extending through the outer shell and/or compression inner. The or each ventilation opening may be covered in a permeable material, such as a mesh. Alternatively, or additionally, the or each opening may comprise a plurality of air channels. The or each ventilation opening may have an outer rim which may be raised from the surface of the walker. The or each ventilation opening may be disposed such that it points in a particular direction. For example, the or each opening may be raised from the surface and may point towards the front (i.e. the toe-end) of the walker. In this embodiment, when the leg is moved forward, air is directed into the forward-facing ventilation openings to thereby ventilate the walker as the patient walks.

The walker may comprise one or more fastening, which is arranged, in use, to releasably bind a subject's injured limb in the walker. The fastening may also serve to provide a degree of compression to the patient's foot, ankle, and/or lower leg. The walker may comprise a fastening at the front of the foot, across the dorsum of the instep and/or across the front of the leg. The or each fastening is preferably adjustable. The fastening preferably allows a straightforward means of rapid adjustment of the tightness of the walker about the limb. For example, this may allow the patient to easily tighten or loosen the walker to accommodate an increase or decrease in swelling on a localized basis. It is also preferable for the or each fastening to allow the walker to be easily removed for bathing, cleansing and dressing the wound, if required. Preferably, the fastenings should also allow the walker to provide uniform compression over the leg, foot, and ankle areas. In addition, or alternatively, the use of a plurality of fastenings may allow the walker to provide compression that is specific to certain parts of the limb. The fastening may be fastened by means of corresponding sections of hook and eye material, such as Velcro. Alternatively, the fastening may comprise adjustable self-locking tension closure buckles.

The orthopaedic walker may be used for the treatment of lower leg and/or foot injuries.

Thus, according to a second aspect, there is provided an orthopaedic walker according to the first aspect, for use in therapy.

According to a third aspect, there is provided an orthopaedic walker according to the first aspect, for use in treating a foot injury.

For example, the injury may be a bone fracture or a sprained ankle. The orthopaedic walker may be used to promote healing of a metatarsal fracture, or a fracture of another bone of the foot, such as fractures of the talus, calcanius, cuboid, navicular, cuniforms, or phalanges. The metatarsal fracture may be a Jones fracture. The primary uses of the walker are for the treatment of any broken metatarsal injuries and Jones fractures (fifth metatarsal). Alternatively, the walker may also be used for any other treatment where the doctor requires the patient to benefit from an offloaded sole whilst maintaining the lower limb in a cast.

According to a fourth aspect, there is provided a method of treating a foot injury in a subject, the method comprising attaching, to a subject in need of such treatment, an orthopaedic walker according to the first aspect.

In addition, in a further aspect, there is provided a combination compression offloader comprising a compression walker boot with an offloader sole.

The top of the boot can be any height fitment from 3, 4, or 5 cm above the ankle to 2 cm below the knee. The percentage of sole that is offloaded may be variable.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawing, in which:—

FIG. 1 is a schematic side view of one embodiment of a walker according to the invention.

EXAMPLE

Referring to FIG. 1, there is shown an orthopaedic walker 10 having a compression boot portion A, and an offloader sole portion B. The walker 10 can be worn by a subject (not shown) for treating injuries of the lower leg and/or foot.

Throughout this specification, references relating to the orientation of the orthopaedic walker refer to the walker in the upright position, as it would be in use, with the sole of the walker placed on the ground. Thus, unless otherwise stated, references to the 'height' of the walker and similar terms, refer to dimensions in the vertical plane; 'length' and similar terms, refer to the heel to toe dimension; and 'width' and similar terms, refer to the dimension running between the inside and outside of the user's limb. For example, the 'top' of the walker refers to the open section of the walker from which, in use, the limb protrudes. The 'front' or similar terms refer to the portions of the walker which encompass the region of the limb of the user between the toes and shin region of the limb. Similarly, the 'rear' or similar terms refer to the portions of the walker which encompass the heel and/or calf of the user as appropriate.

The walker 10 may be easily fitted around and removed from the lower leg of a subject, while also effectively stabilising and compressing the affected limb. The offloader sole B permits increased weight bearing on the injured limb, which in turn increases the mobility of the injured subject and reduces treatment time and cost.

The compression boot portion A of the walker 10 comprises a compression inner 3, which is encased by an outer shell 4, which in this case is a rigid outer shell. The rigid outer shell 4 comprises an ankle stabilisation section 4a at a lower section thereof, and a leg stabilisation section 4b towards an upper section thereof. The purpose of the rigid outer shell 4 of the boot portion A is to provide strength and stability to the walker 10. For this reason, the rigid outer shell 4 may be formed of a material that is stiff, non-flexible, semi-flexible and/or has any degree of flexibility between these two extremes, as appropriate. In the embodiment of the walker 10 shown in FIG. 1, the rigid outer shell 4 is made of a non-flexible injection-moulded polyurethane.

The ankle stabilisation section 4a of the rigid outer shell 4 offers increased support and stability to the ankle and lower leg, and prevents the subject's heel from slipping backward out of the walker 10. The ankle stabilisation section 4a has a bottom portion that forms part of the sole of the walker 10 and a back portion that extends to encompass the subject's heel. The size and precise shape of the ankle stabilisation section 4a, and in particular, the degree to which it extends up the back of the compression boot portion A may vary depending on the nature of the injury, and the type of stabilisation, compression, and offloading required.

The ankle stabilization section 4a is attached to the leg stabilisation section 4b at a pre-moulded area by glue, though rivets may additionally or alternatively be used. In some embodiments, the ankle and leg stabilisation sections 4a and 4b are formed as a single unit, for example by an injection moulding technique.

The leg stabilisation section 4b of the rigid outer shell 4 has a U-shaped cross section, and extends upwards from the ankle stabilisation section 4a towards the subject's knee. The open front of the leg stabilisation section 4b provides support and stabilisation to the sides and rear of the subject's limb, while allowing the limb to be easily inserted into, and extracted from, the walker 10 without the need for excessive handling and manipulation, which may be painful.

The walker 10 shown in the accompanying FIG. 1 is in the form of a 'high top' boot, the top of which stops just below the subject's knee, for example 2 cm below the knee of the subject. However, it will be appreciated that the top of the walker 10 could terminate further down the subject's shin.

The rigid outer shell 4 surrounds and supports an internal compression inner 3, which provides controlled, uniform compression of the patient's foot, ankle and leg. In the embodiment shown, the compression inner 3 comprises a section of breathable, open pore foam, and an inflatable bladder (not shown), wherein the bladder is positioned between two foam layers for additional cushioning. The compression inner 3 is covered with a loose weave absorbable cotton fabric. In alternative embodiments, the fabric may be a natural fabric, or synthetic fabric such as nylon or Lycra, or a combination or different types of fabrics may be used. The compression inner 3 is attached to the outer shell 4 by means of a plurality of patches of Velcro-type nylon hooks on the inner surface of the outer shell 4, which engage with the covering fabric of the compression inner 3 and stop it slipping within the boot. Thus, the compression inner 3 is removable from the outer shell and may be worn in isolation from the outer shell 4, for instance when resting.

The breathable, open pore foam material of the compression inner 3 is composed of soft ethylene vinyl acetate. In general, any suitable material may be used, provided that the foam liner is breathable to a certain extent, because this provides ventilation to the limb, and reduces the overall weight of the walker 10. The bladder is constructed of a resilient urethane material. A rubber or SPANDEX material may alternatively be used, for example, with a urethane laminate coating on the inside.

In use, after the limb is inserted into the walker 10, the bladder may be inflated until a comfortable, compressive fit is provided around the injured limb. To inflate the bladder, a tube is securely inserted into an opening in the bladder and connected to a small manual pump bulb 1a. The bladder also comprises a valve 1b for retaining air and for selective deflation.

The walker 10 comprises a plurality of adjustable straps or fastenings 2, 5, 6 at different height positions. The fastenings 2, 5, 6 each function to releasably bind the walker 10 in position encompassing the injured limb. The purpose of the fastenings is to provide a uniform or variable compression over the full extent of the compression boot portion A from the lower leg through the ankle and across the dorsum of the patient.

The forward-most strap 6 disposed towards the bottom of the walker 10 is used to hold the forefoot in a conventional manner. Strap 5 is disposed above strap 6 and extends across the dorsum of the instep, and is used to pull the top of the foot down against the offloader sole B and back against the ankle stabilisation section 4a of the walker 10. Strap 2 is disposed above strap 6 and extends across the front of the leg and holds the leg securely within the leg stabilisation section 4b of the walker 10. Any of the straps 2, 5, 6 may comprise a single strap or a plurality of straps which may be adjacently situated in positions corresponding to those shown in the accompanying FIGURE. In other embodiments, the straps may be distributed in alternative positions.

Any suitable type of fastening may be used. Generally, the fastening should be capable of being tightened or loosened depending on the condition of the limb and the treatment required at different stages of the healing process. The fastenings preferably allow a straightforward means of rapid adjustment. For example, this may allow the patient to easily tighten or loosen the walker 10 to accommodate an increase or decrease in swelling on a localized basis. It is also preferable for the fastenings to allow the walker 10 to be easily removed for bathing, cleansing and dressing the wound if required.

In the embodiment shown, the straps are fastened by means of corresponding sections of hook and eye material, such as Velcro. In particular, the straps comprise a length of material that is permanently attached to one end to one side of the boot portion. The opposite end of the strap is a section of material comprising a number of nylon hooks, and in the centre of the strap, there is a section of material comprising a number of loops, configured to receive the nylon hooks. The straps may be securely and permanently affixed to the boot portion by being securely affixed to a collar. The collar is constructed from a high-strength plastic and is firmly attached to the rigid outer shell 4 of the walker 10, by means of ultrasonic welding. On the opposite side of the opening at the front of the compression boot portion A, is located a second collar. In order to fasten the strap, the loose end is passed through the second collar, and is then folded back so that the hook portion of the strap may be adjustably attached to the loop portion.

The offloader sole portion B consists of an inner sole, a mid-sole 7a and a wedge-shaped undersole 7b, and is attached to the base of the rigid outer shell 4 of the compression boot portion A of the walker 10. By virtue of this arrangement, the walker 10 is externally offloaded. That is to say, the walker 10 is not offloaded by means of an offloading system that is internal to the boot, for example, in which sections of the inner sole may be modified to alter pressure distribution across the sole of the foot.

In the embodiment shown, the mid-sole 7a and the wedge-shaped undersole 7b are formed as single section 7. This mid-sole/undersole section 7 is formed from a substantially inflexible, ethylene vinyl acetate material, and is attached to rigid outer shell 4 by means of an adhesive. In addition, or as an alternative, rivets or other metal fastenings may be used.

The mid-sole 7a provides support for the foot, and therefore has a profile that is approximately foot-shaped, but slightly larger. The upper surface of the mid-sole 7a is shaped to receive the rigid outer shell 4 of the compression boot section A of the walker 10.

The upper surface of the mid-sole 7a has an upwardly curved heel portion, a central portion that it relatively flat to provide stability, and a toe portion that curves upwardly again at the apex of the ball area terminating at the end of the toe portion of the walker 10. Over its length, the upper surface of the mid-sole 7a is contoured to provide a better fit for the patient's foot with good stability and comfort. The toe end of the mid-sole 7a extends to surround the front and sides of the toes, thereby protecting the toes. The mid-sole 7a has a circumferential lip or vertical ridge, which functions to retain the inner sole.

Configurations of the walker may be used in the treatment of any condition which requires the limb to be compressed and immobilised, and in which it is desirable to remove the weight bearing load from a portion of the foot. Depending on the nature of the injury, the undersole 7b may be positioned towards the front or rear of the base of the walker 10. In particular, conditions for which the walker is especially suitable include fractures of the small bones of the front of the foot, such as Jones fractures and other metatarsal injuries, and in this case, the undersole 7b is positioned at the heel of the walker, as shown in the accompanying FIG. 1. In particular, in the embodiment shown, the undersole 7b is positioned on the base of the walker 10 such that the narrower end of the wedge is aligned at the heel end of the walker 10. The broader end of the wedge is situated at a position about 60% of the distance towards the toe end of the walker 10.

The upper surface of the undersole 7b is inclined at an acute angle of about 15° with respect to the base surface of the undersole 7b.

In the walker 10 shown in the accompanying FIG. 1, the front and rear faces of the undersole 7b are substantially rounded. In other embodiments, the faces may be flat, concave, or have any other shape.

The undersole 7b is substantially shorter than the midsole 7a. In the embodiment shown, the undersole 7b occupies about 65% of the lower surface area of the mid-sole. In alternative embodiments, the undersole 7b is shaped so that the upper surface is the same size and shape as the mid-sole 7a, but the base of the undersole is formed into the wedge shape similar to that shown in FIG. 1.

The upper surface of the offloader sole portion B at the toe end of the walker 10 is approximately 2.5 cm greater in height that at the heel end.

The inner sole of the walker 10 is retained within the circumferential lip or vertical ridge of the mid-sole 7a. The inner sole is formed in a single section of shock absorbing EVA foam material, and does not comprise, for example, removable sections to facilitate internal offloading.

The invention claimed is:

1. An orthopaedic walker suitable for treating a metatarsal fracture, the walker comprising a compression walker boot and an offloader sole, wherein the compression walker boot comprises a compression inner section and an outer shell, and the offloader sole is externally offloaded and is arranged to promote weight bearing on or towards the heel of the foot of the subject wearing the walker;
   wherein the offloader sole comprises a tapered portion,
   the tapered portion comprising a section having a vertically shallow end disposed at or towards the rear end of the sole and increasing in vertical height to a wide end disposed towards the front end of the sole and wherein the tapered portion section does not extend to the end of the front of the sole, thereby offloading pressure, in use, away from the front of the foot.

2. An orthopaedic walker according to claim 1, wherein the toe end of the mid-sole extends to surround the front and sides of the toes, thereby protecting the toes.

3. An orthopaedic walker according to claim 1, wherein the compression inner section is removeably attached to the internal surface of the outer shell.

4. An orthopaedic walker according to claim 3, wherein the compression inner section comprises an inflatable bladder.

5. A method of treating a foot injury in a subject, the method comprising attaching, to a subject in need of such treatment, an orthopaedic walker according to claim 1.

6. A method according to claim 5, wherein the foot injury comprises a fracture to a bone of the foot.

* * * * *